(12) United States Patent
Band et al.

(10) Patent No.: US 6,348,038 B1
(45) Date of Patent: Feb. 19, 2002

(54) METHOD AND APPARATUS FOR THE MEASUREMENT OF CARDIAC OUTPUT

(75) Inventors: David Marston Band, Surbiton; Nicholas William Fox Linton; Robert Anthony Fox Linton, both of London; Terence Kevin O'Brien, Great Shelford, all of (GB)

(73) Assignee: Monitoring Technology Limited, London (GB)

( * ) Notice: Subject to any disclaimer, the term of this patent is extended or adjusted under 35 U.S.C. 154(b) by 0 days.

(21) Appl. No.: 09/462,073
(22) PCT Filed: Jul. 3, 1998
(86) PCT No.: PCT/GB98/01972
  § 371 Date: Mar. 28, 2000
  § 102(e) Date: Mar. 28, 2000
(87) PCT Pub. No.: WO99/02086
  PCT Pub. Date: Jan. 21, 1999

(30) Foreign Application Priority Data

Jul. 10, 1997 (GB) ............................................. 9714550

(51) Int. Cl.$^7$ ................................................. A61B 5/00
(52) U.S. Cl. ...................... 600/485; 600/526; 600/505
(58) Field of Search ................................ 600/485, 486, 600/500, 526

(56) References Cited

U.S. PATENT DOCUMENTS

| | | | |
|---|---|---|---|
| 5,101,828 A | * 4/1992 | Welkowitz et al. | 600/500 |
| 5,311,872 A | * 5/1994 | Apple | 600/500 |
| 5,390,679 A | 2/1995 | Martin | |
| 5,687,731 A | * 11/1997 | Ragozin et al. | 600/526 |
| 5,865,758 A | * 2/1999 | Louzianine | 600/526 |

FOREIGN PATENT DOCUMENTS

| | | |
|---|---|---|
| EP | 0 818 175 A | 1/1998 |
| WO | WO 92 06633 A | 4/1992 |
| WO | WO 97/24982 A | 7/1997 |

OTHER PUBLICATIONS

Lambert et al., 1989, copy of page from textbook which summarizes Lambert work.

"McDonald's Blood Flow in Arteries", Nichols & O'Rourke, 1998.

Nicholas T. Kouchoukos, Louis C. Sheppard, and Donald A. McDonald, "Estimation of Stroke Volume in the Dog by a Pulse Contour Method", Circulation Research, May 1970.

PCT/GB98/01972, "Improved Method and Apparatus for the Measurement of Cardiac Output".

Michael F. O'Rourke and Albert P. Avolio, "Pulsatile Flow and Pressure in Human Systemic Arteries Studies in Man and in a Multibranched Model of the Human Systemic Arterial Tree", Circulation Research, Mar. 1980.

E.O. Attinger, A. Anne, and D.A. McDonald, "Use of Fourier Series for the Analysis of Biological Systems", Biophysical Journal, vol. 6, 1966.

(List continued on next page.)

Primary Examiner—Robert L. Nasser
(74) Attorney, Agent, or Firm—Bacon & Thomas

(57) ABSTRACT

A method for the measurement of cardiac output in a patient in which the arterial blood pressure waveform of a patient from a blood pressure monitoring device over a period of time is subjected to various transformations and corrections, including a Fourier analysis in order to obtain the modulus of the first harmonic. The nominal stroke volume is then determined from the first harmonic and data relating to the arterial blood pressure and heart rate. The nominal cardiac output is then obtained from the nominal stroke volume.

16 Claims, 3 Drawing Sheets stage 1 — ventricle ejects blood into aorta stage 2 — flow into aorta generates pressure stage 3 — pressure is transmitted to peripheral arteries stage 4 — pressure is measured from peripheral artery

OTHER PUBLICATIONS

John W. Remington, Charles R. Noback, W.F. Hamilton and Jay J. Gold, "Volume Elasticity Characteristics of the Human Aorta and Prediction of the Stroke Volume from the Pressure Pulse", Am. J. Physiol. 153, 298–308, (1948).

Martin, J.F. et al., "Application of Pattern Recognition and Image Classification Techniques to Determine Continuous Cardiac Output from the Arterial Pressure Waveform", IEEE Transactions on Biomedical Engineering, Oct. 1994, XP000556740.

* cited by examiner

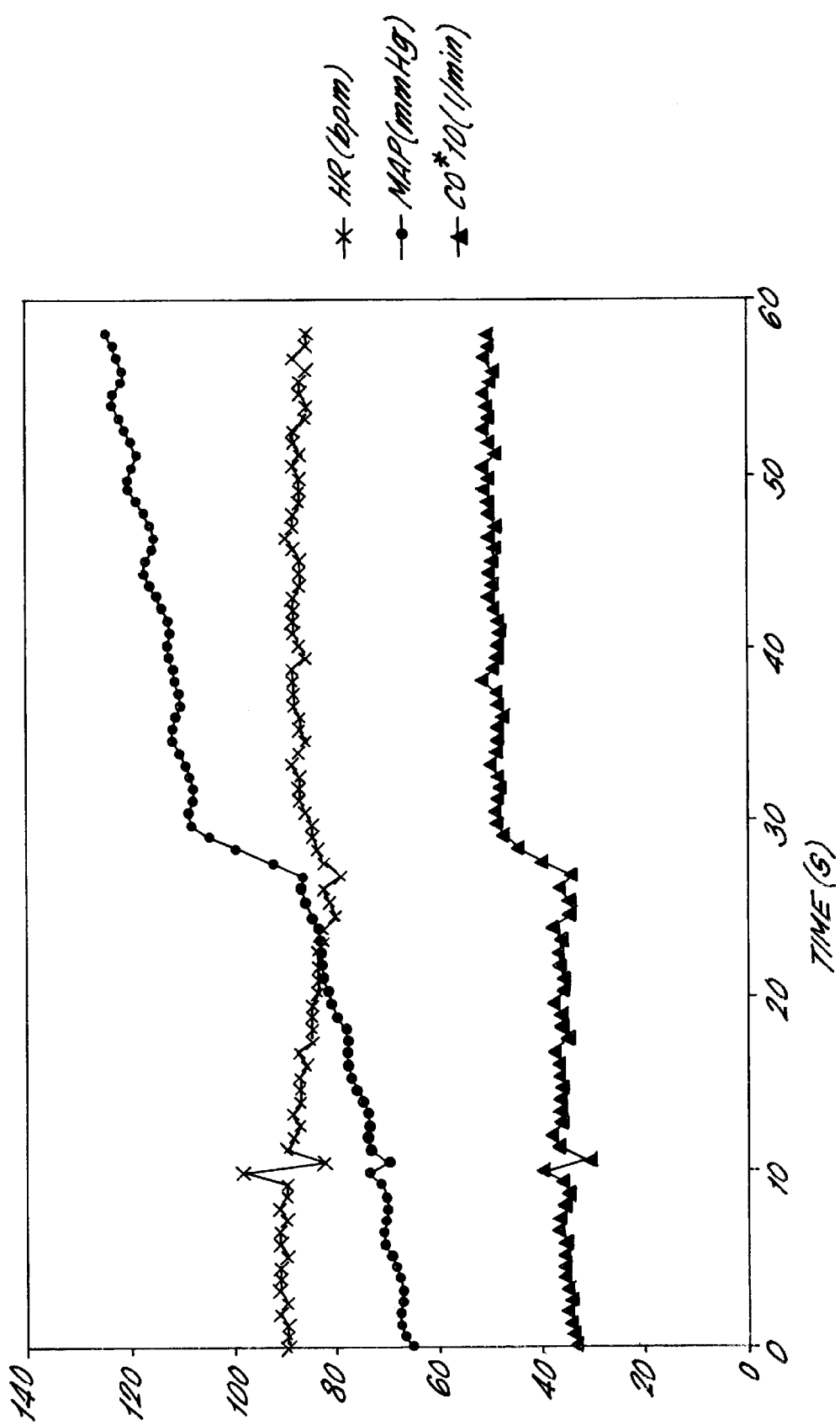
FIG. 3. BEAT-BY-BEAT ANALYSIS

METHOD AND APPARATUS FOR THE MEASUREMENT OF CARDIAC OUTPUT

The present invention relates to an improved method and apparatus for the measurement of cardiac output and in particular to an improved method and apparatus which has a rapid rate of response and good noise rejection.

Cardiac output is an important haemodynamic variable which is defined as the volume of blood that is pumped by the heart per minute.

Blood pressure was first measured in 1750. Since at least 1904 (Erlanger and Hooker, Bull. John Hopkins Hosp. 15:179) it has been suggested that the arterial pulse pressure could be regarded as a rough index to the stroke volume of the heart and, in combination with the heart rate, could provide the cardiac output. This approach was found to be simplistic and has been surpassed by other methods.

Kouchoukos et al. (Estimation of stroke volume in the dog by a pulse contour method, Circ. Res., vol. 26, 5:611–23, 1970) used a method that uses the systolic area to determine stroke volume. The systolic area is the area between the blood pressure and end diastolic pressure during systole. Since 1970 there have been many modifications to the systolic area technique of pulse contour analysis. For example, correction factors such as age, height and weight have been added as well as factors to allow for the changing compliance of the arteries and reflections of the pressure wave from the peripheral circulation.

Even after the correction factors were introduced the results were still not reliable. Currently, pulse contour analysis is not routinely used by clinicians despite the importance of cardiac output. One of the major shortcomings of these methods is their reliance upon measuring morphological features of the blood pressure waveform. In particular, the position of the dicrotic notch, which signifies the closure of-the aortic valve, must be found in order to measure the systolic area. During surgery and intensive care the dicrotic notch may not be detectable or it may be mimicked by other minor waves superimposed upon the pressure waveform.

U.S. Pat. No. 5400793 describes another method for determining the stroke volume from aortic blood pressure in a subject. The method uses a simulation model of the aorta as a transmission line, including a pressure volume relationship for the aorta that is known in the art and supplemented with a Windkessel compliance.

In essence, the pressure recorded in the aorta is used to determine the characteristic impedance of the transmission line model. The simulation is then performed and the parameters of the Windkessel are adapted until the flow calculated in the model is consistent with the pressure in the aorta. The flow is then integrated over the period of systole. Ideally, this method requires a high fidelity transducer positioned in the aorta. Although a method of correcting a pressure measurement in a peripheral artery is mentioned, this method cannot be used with the poor frequency response given by most pressure transducers now routinely in clinical use: in the presence of noise an "anti-resonance filter" cannot recover the information that is lost by the poor quality of these transducers.

None of the aforementioned methods of measuring cardiac output explicitly account for the frequency response of the transducers now in routine clinical use. Lambert et al. (Pressure measurement in diagnostic and therapeutic cardiac catheterisation, eds. Pepine et al., Williams and Wilkins, Baltimore, 283–97) found that with added extension tubes, the response of some measuring systems is accurate (to within 5%) only for frequencies less than 2 Hz.

Finally, Hamilton (The physiology of cardiac output, circulation 8: 527, 1953) suggested that cardiac output could be derived from a patient's blood pressure pulse height following calibration by another device.

It is now accepted in the art that all existing pulse contour methods require calibration for improved accuracy. The present invention is also intended to be used with a calibration device, for example a thermodilution or indicator dilution method. An indicator dilution method is described, for example, in WO93/09427. The method as described in WO93/09427 is highly repeatable and only one single point calibration is required to give the cardiac output. It will be understood, however, that the method of the present invention may be used without calibration in order to show trends in or directions of change of the cardiac output of a patient.

In our co-pending application WO97/24982 we have described an improved method for measuring cardiac output using pulse contour analysis. A non-linear transformation is used to correct for the changing characteristics of the arterial system with pressure and autocorrelation is then used to derive the cardiac output. Although this technique is an improvement over the prior art methods discussed above, there is still a need for a further improved method.

The method described in WO97/24982 was an empirical finding and has given good results in patients undergoing cardiac surgery. The present invention gives results that are numerically similar under normal conditions. However, the frequency response of the pressure measurement system is explicitly accounted for. It is also based upon a stronger theoretical framework which will allow modification to the method to be assessed more easily.

Accordingly, in a first aspect the present invention provides a method for the measurement of cardiac output in a patient, which method comprises the steps of:

(i) recording and storing the arterial blood pressure waveform of a patient from a blood pressure monitoring device over a period of time;

(ii) subjecting the data obtained in step (i) to Fourier analysis in order to obtain the modulus of the first harmonic;

(iii) determining the nominal stroke volume from the modulus of the first harmonic obtained in step (ii) and data relating to the arterial blood pressure and the heart rate; and (iv) obtaining the nominal cardiac output and/or the systemic vascular resistance from data obtained in step (iii).

Step (ii) above is preferably achieved by identifying a period of the waveform obtained in step (i) that contains at least one beat.

Arteries generally have non-linear properties. The above method assumes that the compliance does not vary significantly within the range of blood pressures that occur during a single beat. The compliance at the corresponding mean arterial pressure is preferably used. Alternatively, the blood pressure may be transformed during an initial step which linearises the blood pressure with respect to the arterial compliance.

In a second aspect the present invention provides a method for the measurement of cardiac output in a patient, which method comprises the steps of:

(a) recording and storing the arterial blood pressure waveform of a patient from a blood pressure monitoring device over a period of time;

(b) subjecting the waveform obtained in step (a) to a non-linear transformation that corrects for the variation of the characteristics of the arterial system with pressure;

(c) subjecting the data obtained in step (b) to Fourier analysis in order to obtain the modulus of the first harmonic;

(d) determining the nominal stroke volume from the modulus of the first harmonic obtained in step (c) and data relating to the heart rate and optionally the arterial blood pressure; and (e) obtaining the nominal cardiac output and/or the systemic vascular resistance from data obtained in step (d).

In step (b) the non-linear transformation preferably linearises the pressure with respect to the arterial compliance.

Step (c) is preferably achieved by identifying each beat of the waveform obtained in step (b) that contains at least one beat.

In both aspects of the present invention the heart rate may be determined, for example, using an autocorrelation method as described in WO97/24982, Fourier analysis, filtering techniques on the pressure waveform and/or edge detection or any other suitable technique. The same data is preferably used to determine the nominal stroke volume and the heart rate.

In both aspects of the present invention the nominal cardiac output is preferably obtained by multiplying the nominal stroke volume by the heart rate. If this is done beat-by-beat, then stroke volume and heart rate data are obtained for a number of beats. It will be appreciated that this data may be used in a number of ways to derive the nominal cardiac output and the systemic vascular resistance.

In carrying out either of the methods of the present invention the patient's arterial blood pressure is monitored continuously by conventional means from, for example, the aorta, the brachial artery or radial artery. Accordingly, the patient's arterial blood pressure may be monitored using an arterial catheter with a transducer system or a non-invasive method. The output from the pressure measuring device preferably provides the blood pressure for at least one beat. It is preferably an analogue or digital signal with a sample rate great enough to accurately reproduce the first harmonic of the waveform, for a period of up to 10 seconds, preferably for a period of up to four seconds. The blood pressure data is generally analyzed on a beat-by-beat basis.

Fourier analysis may be used to determine the harmonic components of a complex wave and is described in detail in many mathematical and physics textbooks. Fourier analysis enables a periodic function to be represented by a Fourier series of trigonometric functions, thus:

$$f(t)=a_0/2+a_1\cos(2\pi t/T)+a_2\cos(4\pi t/T)+\ldots+b_1\sin(2\pi t/T)+b_2\sin(4\pi t/T)+\ldots$$

where $a_0$, $a_1$, $b_1$ and $b_2$ are constants, t is the time and T is the period.

The use of Fourier analysis in the present invention assumes that the signal is periodic and that the arterial system is linear. In reality, the heart may beat irregularly and there are non-linearities, for example the arteries become stiffer as arterial pressure increases. However, the errors that this introduces have been examined by other workers who found them to be small (E. O. Attinger, A. Anné and D. A. MacDonald, "Use of Fourier series for the Analysis of Biological Systems", Biophysical Journal, Volume 6, 1966).

It is possible to reduce the errors introduced by the reduction of arterial compliance with increases in arterial pressure. Accordingly, in the second aspect of the present invention a non-linear transformation of the blood pressure waveform obtained in step (a) is carried out to correct for the variation of the characteristics of the arterial system with pressure. The corrected waveform is then subjected to Fourier analysis.

As mentioned above, the pressure waveform obtained in step (b) of the second is transformed, preferably via a 'look-up' table, with the mean of the data then being found and subtracted, into data which represents the pressure-volume relationship of the arterial system. The basic approximation to a look up arterial system. The basic approximation to a look up table is known in the art. A series of pressure-volume curves is described in Remington et al., "Volume elasticity characteristics of the human aorta and prediction of the stroke volume from the pressure pulse", Am. J. Physiol 153: 298–308,1948.

The nominal cardiac output may be obtained using the nominal stroke volume and heart rate. The nominal cardiac output may found, for example, by multiplying the nominal stroke volume by the heart rate. If more than one beat is used to calculate the nominal cardiac output then it may be calculated as the sum of the stroke volumes divided by the sum of the durations of each beat. It will be understood that the nominal stroke volume and the nominal cardiac output are uncalibrated and may be converted into calibrated data if desired. This is performed by multiplying the nominal stroke volume by a calibration factor to give the true stroke volume, as found by another method. The cardiac output may then be calculated from the true stroke volume and heart rate. The nominal systemic vascular resistance (SVR) may be calculated by dividing the mean arterial pressure by the nominal cardiac output. A true value may also be obtained from the true cardiac output.

The present invention gives a close to real-time analysis of rapidly changing events. For example, the method of the present invention may be used to monitor changes in the cardiac output following the administration of fluids, or to set a pacemaker to an optimal rate, or to determine when administration of a vasoactive drug may be required.

In carrying out the second method of the present invention steps (a), (d) and (e) correspond generally to steps (i), (iii) and (iv) of the first method as discussed herein.

The methods of the present invention may be applied to periods of blood pressure data greater than one heart beat or to single heart beats if they can be identified separately, i.e. a beat-by-beat analysis. Methods for identifying single heart beats are known in the art.

Apparatus for carrying out the present invention may comprise any suitably programmed computer such as an IBM compatible computer or a Macintosh computer which is able to acquire data from the blood pressure measurement device or monitor. It may also be integrated with software and hardware for performing other tasks. For example, the device may be capable of carrying out the present invention as well as the method used for calibration or other monitoring tasks. The computer programme running on the computer may then either display the results on a visual display unit or can output this information to some other device.

Accordingly, in a further aspect the present invention provides an apparatus for the measurement of cardiac output in a patient, which comprises:

(1) means for recording and storing the arterial blood pressure waveform of a patient from a blood pressure monitoring device over a period of time;

(2) means for Fourier analysis of the arterial blood pressure waveform to obtain the modulus of the first harmonic;

(3) means for deriving the nominal stroke volume from the modulus of the first harmonic and data relating to the arterial blood pressure and the heart rate; and (4) means for calculating the nominal cardiac output and/or the systemic vascular resistance.

Alternatively, in a still further aspect the present invention provides an apparatus for the measurement of cardiac output in a patient, which method comprises the steps of:

(A) means for recording and storing the arterial blood pressure waveform of a patient from a blood pressure monitoring device over a period of time;

(B) means for transforming the arterial blood pressure waveform to correct for the variation of the characteristics of the arterial system with pressure;

(C) means for the Fourier analysis of the transformed data to obtain the modulus of the first harmonic of the waveform;

(D) means for determining the nominal stroke volume from the modulus of the first harmonic and data relating to the heart rate and optionally the arterial blood pressure; and (E) means for calculating the nominal cardiac output and/or the systemic vascular resistance.

The present invention will be further described, by way of example, with reference to the accompanying drawings in which:

FIG. 3 illustrates the use of the method of the present invention in determining cardiac output in a patient undergoing heart surgery.

The current invention is based upon a model that relates the first harmonic of the measured blood pressure to the first harmonic of the flow in the aorta. A relationship between the first harmonic of the flow in the aorta and the mean flow in the aorta is assumed. The stroke volume for each beat can then be calculated by multiplying the mean flow by the duration of each beat. The cardiac output can be calculated over any required period by summing he stroke volumes over that period and dividing by the duration of the period. A period of 15 seconds is typical for this purpose.

Figure 1:
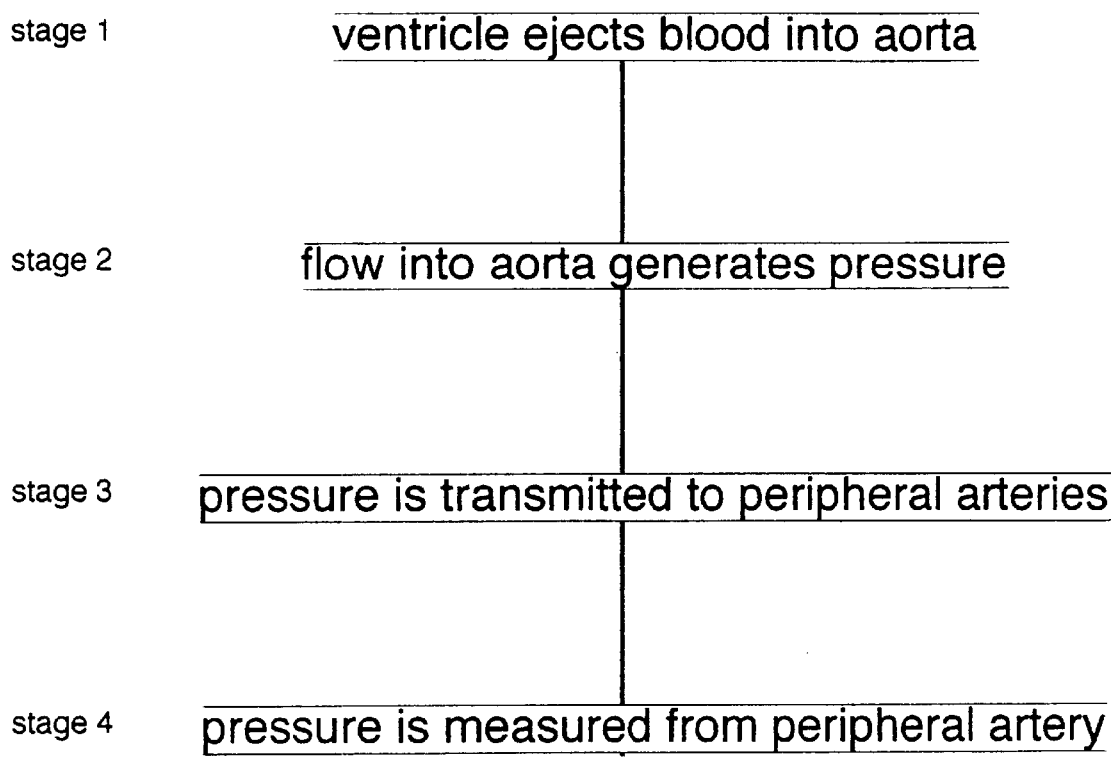
FIG. 1 is a diagram of the physical processes which relate the ejection of blood from the left ventricle to the blood pressure reading from the measurement device.

FIG. 1 describes the physical processes which relate the ejection of blood from the left ventricle to the blood pressure reading from the measurement device. These are described in four stages. Stage 1—the ventricle creates a flow into the aorta, this rises to a peak during systole and is approximately zero during diastole (assuming a competent aortic valve). Stage 2—the flow from the ventricle creates a pressure in the ascending aorta, the pressure-flow relationship is the ascending aorta input impedance. Stage 3—the pressure in the aorta is transmitted to the peripheral arteries. Stage 4—the peripheral artery pressure (e.g. radial artery) is measured, however, the measurement process introduces distortion. The current invention uses approximations to each stage in order to relate the first harmonic of the blood pressure to the stroke volume ejected by the heart. These approximations are described below.

Figure 2:
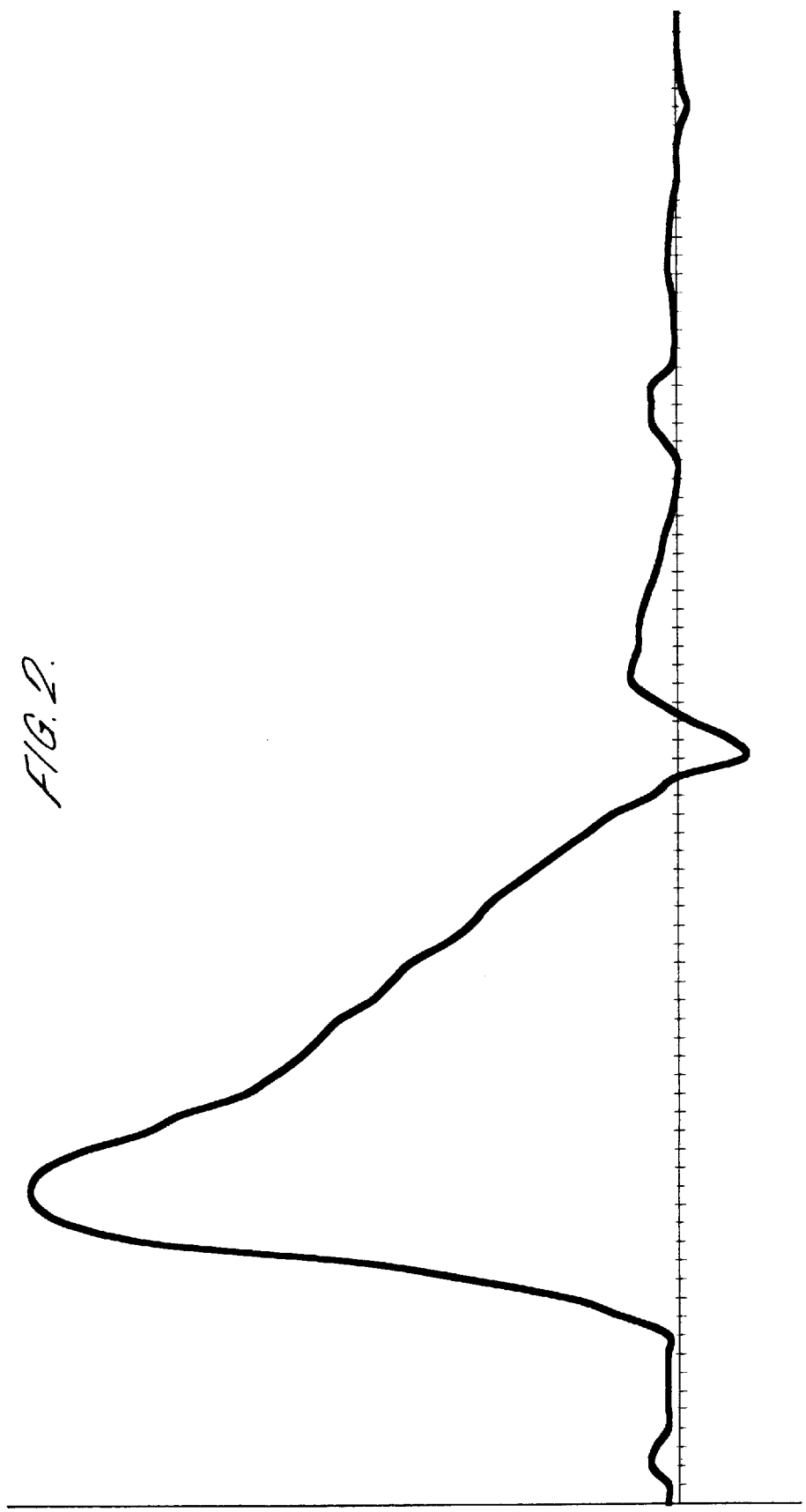
FIG. 2 shows a typical example of the aortic flow for one beat.

Stage 1 FIG. 2 shows a typical example of the aortic flow for one beat. During systole the flow increases after the left ventricle starts to contract. The flow rises to a peak and then falls. The flow then reverses for a short period which causes the aortic valve to close. This prevents blood from returning to the relaxed ventricle. The basic morphology of the flow waveform is restricted by these physical processes. Thus there is a predictable relationship between the first harmonic of the aortic flow and mean aortic flow. As the heart rate increases, the duration of systole occupies a greater proportion of the cardiac cycle. This results in the ratio of the mean flow to the first harmonic of the flow falling as the heart rate rises. Thus, the first harmonic can be related to the mean flow.

Stage 2 The aortic input impedance relates the flow to the pressure, in the frequency domain. The present invention uses an approximation for the aortic impedance in the range of frequencies that may occur for the first harmonic of the pressure/flow waveform i.e. the heart rate. This is 30–150 beats per minute or 0.5–2.5 Hz. The approximation also allows for changes in impedance that occur as the systemic vascular resistance (SVR) and arterial pressure change.

The relationship between aortic input impedance and frequency has been studied in vivo by many other workers. In particular, O'Rourke and Aviolo found good agreement between measurements made in a man and a 128 segment numerical model (M. F. O'Rourke and A. P. Aviolo, 'Pulsatile flow and pressure in human systemic arteries: studies in man and in a multibranched model of the human systemic arterial tree', Circulation Research, vol. 43, no. 3, March 1980). This model is well approximated by impedance=1÷frequency for the range 0.5–2.5 Hz.

Since the work of Aviolo and O'Rourke others have developed the model to account for changes in SVR. As the SVR increases the impedance at the frequency of the first harmonic (for normal heart rates) also increases. In addition to this the blood pressure also affects aortic input impedance; at high blood pressures the arteries are less compliant.

As well as the effects described above, arterial dilatation can also affect the aortic input impedance. This is due to a reduction in wave reflection from the peripheral circulation. In order to account for the resulting change in impedance an augmentation index may be calculated. This gives an indication of the magnitude of wave reflection and a method for doing this is reviewed in McDonald's Blood Flow in Arteries, Nichols and O'Rourke, London, Arnold 1998.

In order to approximate the aortic impedance (at the frequency of the first harmonic of the blood pressure waveform) a relationship is used that depends upon frequency, SVR, and mean blood pressure. The approximation may be further improved by calculation of an augmentation index.

Stage 3 As the pressure waveform is transmitted from the aorta to the peripheral arteries it is distorted. This occurs because of arterial branching, changes in the characteristic impedance of the arteries, and reflection from the periphery caused by an impedance mismatch between the arteries and the arterioles. However, reflection is more predictable at low frequencies.

Stage 4 The performance of catheter-manometer systems (which are used to measure blood pressure clinically) is described in McDonald's Blood Flow in Arteries, Nichols & O'Rourke, London, Arnold, 1998. The present invention is intended for use at heart rates of 0.5–2.5 Hz. It is important that the measurement system has a frequency response that is sufficient to reproduce the fundamental frequency of the blood pressure waveform i.e. the frequency of the heart rate. If the measurement system is only capable of reproducing frequencies up to less than 2.5 Hz then the system may still be used if the heart rate remains below the maximum frequency that can be reproduced. The formula used to relate the blood pressure data to the stroke volume is required to account for the relationships described by stages 1 & 2. No explicit correction is usually required for stages 3 and 4 because their physical effects upon frequencies less than 2.5 Hz are negligible.

An example of an equation which may be used is:

$$\text{nominal mean flow} = \frac{\text{modulus of first harmonic of blood pressure waveform}}{e^{+0.0092 \times MAP}}$$

$$\text{nominal stroke volume} = \frac{\text{modulus of first harmonic of blood pressure waveform}}{e^{+0.0092 \times MAP} \times HR}$$

where e is the base of natural logarithms, MAP is the mean arterial blood pressure and HR is the heart rate.

Thus, the nominal cardiac output may be calculated directly from the modulus of the first harmonic of the blood pressure waveform and the blood pressure, and optionally the heart rate. For example:

$$\text{nominal cardiac output} = \frac{\text{modulus of first harmonic of blood pressure waveform}}{e^{+0.0092 \times MAP}}$$

Referring now to FIG. 3, a beat-by-beat analysis of the patient's heart rhythm during heart surgery is charted as the trace labelled HR. The mean arterial blood pressure is also charted as the trace MAP. The heart was in nodal rhythm—a condition in which abnormal electrical activity causes the heart to function inefficiently. About twenty-seven seconds into the trace the heart changed to sinus rhythm (normal). The immediate increase in the performance of the heart is indicated by the change in mean arterial pressure over the next four beats. The derived cardiac output also shows an immediate increase confirming that the cause of the increase in pressure was due to better cardiac performance (rather than an increase in peripheral resistance).

We claim:

1. A method for the measurement of cardiac output in a patient, which method comprises the steps of:

(i) recording and storing the arterial blood pressure waveform of a patient from a blood pressure monitoring device over a period of time;

(ii) subjecting the data obtained in step (i) to Fourier analysis in order to obtain the modulus of the first harmonic;

(iii) determining the nominal stroke volume from the modulus of the first harmonic obtained in step (ii) and data relating to the arterial blood pressure and the heart rate; and (iv) obtaining the nominal cardiac output and/or the systemic vascular resistance from data obtained in step (iii).

2. A method as claimed in claim 1 wherein the arterial blood pressure is recorded and stored in step (i) for a period of up to ten seconds.

3. A method as claimed in claim 2 wherein the arterial blood pressure is recorded and stored in step (i) for a period of up to four seconds.

4. A method as claimed in claim 1 wherein the arterial blood pressure is analysed on a beat-by-beat basis.

5. A method as claimed in claim 1, wherein the nominal stroke volume is obtained from the following equation:

$$\text{nominal stroke volume} = \frac{\text{modulus of first harmonic of blood pressure waveform}}{e^{+0.0092 \times MAP} \times HR}$$

where e is the base of natural logarithms and MAP is the mean arterial blood pressure.

6. A method as claimed in claims 1, wherein an augmentation index is included in the calculation of the nominal stroke volume in step (iii).

7. A method as claimed in claim 1 wherein the nominal cardiac output is obtained by multiplying the nominal stroke volume by the heart rate.

8. A method for the measurement of cardiac output in a patient, which method comprises the steps of:

(a) recording and storing the arterial blood pressure waveform of a patient from a blood pressure monitoring device over a period of time;

(b) subjecting the waveform obtained in step (a) to a non-linear transformation that corrects for the variation of the characteristics of the arterial system with pressure;

(c) subjecting the data obtained in step (b) to Fourier analysis in order to obtain the modulus of the first harmonic;

(d) determining the nominal stroke volume from the modulus of the first harmonic obtained in step (c) and data relating to the heart rate and optionally the arterial blood pressure; and (e) obtaining the nominal cardiac output and/or the systemic vascular resistance from data obtained in step (d).

9. A method as claimed in claim 7 wherein the arterial blood pressure is recorded and stored in step (a) for a period of up to ten seconds.

10. A method as claimed in claim 9 wherein the arterial blood pressure is recorded and stored in step (a) for a period of up to four seconds.

11. A method as claimed in claim 8 wherein the arterial blood pressure is analysed on a beat-by-beat basis.

12. A method as claimed in claim 8 wherein the transformation in step (b) is effected using a look up table, with the mean of the data then being found and subtracted.

13. A method as claimed in claim 8 wherein the nominal stroke volume is obtained from the following equation:

$$\text{nominal stroke volume} = \frac{\text{modulus of first harmonic of blood pressure waveform}}{e^{+0.0092 \times MAP} \times HR}$$

14. A method as claimed in claim 8 wherein an augmentation index is included in the calculation of the nominal stroke volume in step (iii).

15. An apparatus for the measurement of cardiac output in a patient, which comprises:

(1) means for recording and storing the arterial blood pressure waveform of a patient from a blood pressure monitoring device over a period of time;

(2) means for Fourier analysis of the arterial blood pressure waveform to obtain the modulus of the first harmonic;

(3) means for deriving the nominal stroke volume from the modulus of the first harmonic and data relating to the arterial blood pressure and the heart rate; and (4) means for calculating the nominal cardiac output and/or the systemic vascular resistance.

16. An apparatus for the measurement of cardiac output in a patient, which method comprises the steps of:
(A) means for recording and storing the arterial blood pressure waveform of a patient from a blood pressure monitoring device over a period of time;
(B) means for transforming the arterial blood pressure waveform to correct for the variation of the characteristics of the arterial system with pressure;
(C) means for the Fourier analysis of the transformed data to obtain the modulus of the first harmonic of the waveform;
(D) means for determining the nominal stroke volume from the modulus of the first harmonic and data relating to the heart rate and optionally the arterial blood pressure; and
(E) means for calculating the nominal cardiac output and/or the systemic vascular resistance.

* * * * *